United States Patent
Mauge et al.

(10) Patent No.: US 8,192,366 B2
(45) Date of Patent: Jun. 5, 2012

(54) METHOD FOR MEASURING VENTRICULAR PRESSURE USING A PRESSURE SENSING VALVE

(75) Inventors: Christophe Mauge, Doylestown, PA (US); Alan J. Dextradeur, Franklin, MA (US); Daniel J. McCusker, Bridgewater, MA (US); Stefan Meyer, Breidenbach (DE); Volker Boedecker, Hannover (DE); Robert G. Kraus, Attleboro, MA (US); Max G. Ostermeier, Hannover (DE)

(73) Assignee: Codman & Shurtleff, Inc., Raynham, MA (US)

( * ) Notice: Subject to any disclaimer, the term of this patent is extended or adjusted under 35 U.S.C. 154(b) by 625 days.

(21) Appl. No.: 12/372,313

(22) Filed: Feb. 17, 2009

(65) Prior Publication Data
US 2009/0156960 A1     Jun. 18, 2009

Related U.S. Application Data

(62) Division of application No. 10/907,665, filed on Apr. 11, 2005, now Pat. No. 7,510,533.

(60) Provisional application No. 60/661,758, filed on Mar. 15, 2005.

(51) Int. Cl.
A61B 5/02     (2006.01)
A61B 5/00     (2006.01)

(52) U.S. Cl. .......................... 600/488; 600/486; 600/561

(58) Field of Classification Search .................. 600/486, 600/488, 561
See application file for complete search history.

(56) References Cited

U.S. PATENT DOCUMENTS

| | | | |
|---|---|---|---|
| 3,886,948 A | 6/1975 | Hakim | |
| 4,127,110 A | 11/1978 | Bullara | |
| 4,237,900 A | 12/1980 | Schulman et al. | |
| 4,332,255 A | 6/1982 | Hakim et al. | |
| 4,385,636 A * | 5/1983 | Cosman | 600/561 |
| 4,387,715 A | 6/1983 | Hakim et al. | |
| 4,494,950 A | 1/1985 | Fischell | |

(Continued)

FOREIGN PATENT DOCUMENTS

EP     0115548     8/1984

(Continued)

OTHER PUBLICATIONS

Office Action dated Oct. 15, 2007 issued for U.S. Appl. No. 10/907,664.

(Continued)

*Primary Examiner* — Miranda Le
*Assistant Examiner* — Tiffany Weston
(74) *Attorney, Agent, or Firm* — Nutter McClennen & Fish LLP

(57) ABSTRACT

A pressure sensing catheter having a pressure sensor and an antenna that is coupled to the pressure sensor, e.g., by a connector, are provided. The pressure sensor can be adapted to measure a pressure surrounding the catheter, and the antenna can be adapted to telemetrically communicate the measured pressure to an external device. In an exemplary embodiment, the antenna, pressure sensor, and/or connector are hermetically sealed, e.g., by the catheter and/or a coating, to prevent the antenna, pressure sensor, and connector from coming into contact with fluid, thereby allowing the catheter to be permanently implanted or otherwise used for long term use. Exemplary methods for manufacturing and using pressure sensing catheters are also provided.

10 Claims, 13 Drawing Sheets

U.S. PATENT DOCUMENTS

| | | | |
|---|---|---|---|
| 4,551,128 | A | 11/1985 | Hakim et al. |
| 4,593,703 | A | 6/1986 | Cosman |
| 4,595,390 | A | 6/1986 | Hakim et al. |
| 4,611,578 | A | 9/1986 | Heimes |
| 4,615,691 | A | 10/1986 | Hakim et al. |
| 4,625,730 | A | 12/1986 | Fountain et al. |
| 4,660,568 | A | 4/1987 | Cosman |
| 4,718,425 | A | 1/1988 | Tanaka et al. |
| 4,723,556 | A | 2/1988 | Sussman |
| 4,772,257 | A | 9/1988 | Hakim et al. |
| 4,787,886 | A | 11/1988 | Cosman |
| 4,841,977 | A | 6/1989 | Griffith et al. |
| 4,850,358 | A | 7/1989 | Millar |
| 4,885,002 | A | 12/1989 | Watanabe et al. |
| 5,005,584 | A | 4/1991 | Little |
| 5,009,644 | A | 4/1991 | McDonald |
| 5,252,962 | A | 10/1993 | Urbas et al. |
| 5,265,606 | A | 11/1993 | Kujawski |
| 5,321,989 | A | 6/1994 | Zimmer et al. |
| 5,385,514 | A | 1/1995 | Dawe |
| 5,417,235 | A | 5/1995 | Wise et al. |
| 5,431,057 | A | 7/1995 | Zimmer et al. |
| 5,630,836 | A | 5/1997 | Prem et al. |
| 5,704,352 | A * | 1/1998 | Tremblay et al. ............ 600/300 |
| 5,795,307 | A | 8/1998 | Krueger |
| 5,836,886 | A | 11/1998 | Itoigawa et al. |
| 5,873,840 | A | 2/1999 | Neff |
| 5,928,182 | A | 7/1999 | Kraus et al. |
| 5,957,912 | A | 9/1999 | Heitzmann |
| 6,083,174 | A | 7/2000 | Brehmeier-Flick et al. |
| 6,113,553 | A | 9/2000 | Chubbuck |
| 6,120,457 | A | 9/2000 | Coombes et al. |
| 6,123,454 | A | 9/2000 | Canfield et al. |
| 6,208,254 | B1 | 3/2001 | McQueen et al. |
| 6,210,346 | B1 | 4/2001 | Hall et al. |
| 6,248,080 | B1 | 6/2001 | Miesel et al. |
| 6,264,611 | B1 | 7/2001 | Ishikawa et al. |
| 6,264,612 | B1 | 7/2001 | McConnell et al. |
| 6,316,522 | B1 | 11/2001 | Loomis et al. |
| 6,533,733 | B1 | 3/2003 | Ericson et al. |
| 6,537,232 | B1 | 3/2003 | Kucharczyk et al. |
| 6,626,902 | B1 | 9/2003 | Kucharczyk et al. |
| 6,636,769 | B2 | 10/2003 | Govari et al. |
| 6,731,976 | B2 | 5/2004 | Penn et al. |
| 6,770,030 | B1 | 8/2004 | Schaupp et al. |
| 6,855,115 | B2 | 2/2005 | Fonseca et al. |
| 6,974,422 | B1 | 12/2005 | Millar |
| 7,435,229 | B2 | 10/2008 | Wolf |
| 7,613,497 | B2 | 11/2009 | Govari et al. |
| 2002/0035331 | A1 | 3/2002 | Brockway et al. |
| 2002/0077553 | A1 | 6/2002 | Govari et al. |
| 2002/0077671 | A1 | 6/2002 | Govari et al. |
| 2002/0087059 | A1 | 7/2002 | O'keefe |
| 2002/0099428 | A1 | 7/2002 | Kaufman |
| 2002/0151816 | A1 | 10/2002 | Rich et al. |
| 2003/0032915 | A1 | 2/2003 | Saul |
| 2003/0135110 | A1 | 7/2003 | Leussler |
| 2003/0135147 | A1 | 7/2003 | Rosenberg et al. |
| 2003/0187411 | A1 | 10/2003 | Constantz |
| 2003/0216666 | A1 | 11/2003 | Ericson et al. |
| 2004/0073137 | A1 | 4/2004 | Lloyd et al. |
| 2004/0147871 | A1 | 7/2004 | Burnett |
| 2004/0193021 | A1 | 9/2004 | Zdeblick et al. |
| 2005/0043669 | A1 | 2/2005 | Rosenberg |
| 2005/0043670 | A1 | 2/2005 | Rosenberg |
| 2005/0043699 | A1 | 2/2005 | Minato |
| 2005/0187487 | A1 | 8/2005 | Azizkhan et al. |
| 2005/0187488 | A1 * | 8/2005 | Wolf ........................... 600/561 |
| 2005/0197585 | A1 | 9/2005 | Brockway et al. |
| 2005/0277839 | A1 | 12/2005 | Alderman et al. |
| 2006/0009699 | A1 | 1/2006 | Roteliuk et al. |
| 2006/0020239 | A1 | 1/2006 | Geiger et al. |
| 2006/0211944 | A1 | 9/2006 | Mauge et al. |
| 2006/0211945 | A1 | 9/2006 | Mauge et al. |
| 2006/0211946 | A1 | 9/2006 | Mauge et al. |
| 2007/0167867 | A1 | 7/2007 | Wolf |
| 2008/0139959 | A1 | 6/2008 | Miethke et al. |
| 2008/0214983 | A1 | 9/2008 | Mauge et al. |

FOREIGN PATENT DOCUMENTS

| | | |
|---|---|---|
| EP | 1312302 | 5/2003 |
| EP | 1389477 | 2/2004 |
| EP | 1491137 | 12/2004 |
| EP | 1491137 A2 | 12/2004 |
| JP | 3-090168 A | 4/1991 |
| JP | 4-141139 A | 5/1992 |
| JP | 7-231879 A | 9/1995 |
| JP | 2005-052642 A | 3/2005 |
| JP | 2005-058775 A | 3/2005 |
| WO | 9105575 | 5/1991 |
| WO | 2006117123 | 11/2006 |
| WO | 2007081741 A2 | 7/2007 |

OTHER PUBLICATIONS

Office Action dated Mar. 21, 2008 issued for U.S. Appl. No. 10/907,663.
Office Action dated Jul. 7, 2008 issued for U.S. Appl. No. 10/907,664.
Office Action dated Jul. 24, 2007 issued for U.S. Appl. No. 10/907,664.
Office Action dated Jul. 15, 2008 issued for U.S. Appl. No. 10/907,665.
Office Action dated Jan. 10, 2008 issued for U.S. Appl. No. 10/907,664.
Office Action dated Feb. 8, 2007 issued for U.S. Appl. No. 10/907,664.
Office Action dated Dec. 4, 2007 issued for U.S. Appl. No. 10/907,665.
J.S. Kronin, et al., "Long-term testing of intracranial pressure monitoring device," J. Neurosurg; vol. 93:852-858 (2000).
"Telemetric Integrated Pressure Sensors," product data sheet of Institut Mikroelektronische Schaultungen und Systeme, :1 (Sep. 2002).
"Surface Micromachined Pressure Sensor Technologies," product data sheet of Institut Mikroelektronische Schaultungen und Systeme, :1-2 (Feb. 2002).
"Sensor Transponder for Pressure and Temperature," data sheet of Institut Mikroelektronische Schaultungen und Systeme, :1-2 (Feb. 2000).
Office Action dated Jan. 29, 2007 issued for U.S. Appl. No. 10/907,663.
Office Action dated Jul. 30, 2007 issued for U.S. Appl. No. 10/907,663.
Office Action dated Oct. 18, 2007 issued for U.S. Appl. No. 10/907,663.

* cited by examiner

METHOD FOR MEASURING VENTRICULAR PRESSURE USING A PRESSURE SENSING VALVE

CROSS-REFERENCE TO RELATED APPLICATIONS

The present application is a divisional of U.S. application Ser. No. 10/907,665, filed on Apr. 11, 2005 and entitled "Pressure Sensing Valve," which claims priority to U.S. Provisional Patent Application No. 60/661,758, filed on Mar. 15, 2005 and entitled "Pressure Sensing Methods and Devices," which are hereby incorporated by reference in their entireties.

FIELD OF THE INVENTION

The present invention relates to ventricular catheters, and in particular to a catheter device having a pressure sensor disposed therein and methods for using the same.

BACKGROUND OF THE INVENTION

Hydrocephalus is a neurological condition that is caused by the abnormal accumulation of cerebrospinal fluid (CSF) within the ventricles, or cavities, of the brain. CSF is a clear, colorless fluid that is primarily produced by the choroid plexus and surrounds the brain and spinal cord. CSF constantly circulates through the ventricular system of the brain and is ultimately absorbed into the bloodstream. CSF aids in the protection of the brain and spinal cord. Because CSF keeps the brain and spinal cord buoyant, it acts as a protective cushion or "shock absorber" to prevent injuries to the central nervous system.

Hydrocephalus, which affects children and adults, arises when the normal drainage of CSF in the brain is blocked in some way. Such blockage can be caused by a number of factors, including, for example, genetic predisposition, intra-ventricular or intra-cranial hemorrhage, infections such as meningitis, head trauma, or the like. Blockage of the flow of CSF consequently creates an imbalance between the amount of CSF produced by the choroid plexus and the rate at which CSF is absorbed into the bloodstream, thereby increasing pressure on the brain, which causes the ventricles to enlarge.

Hydrocephalus is most often treated by surgically inserting a shunt system that diverts the flow of CSF from the ventricle to another area of the body where the CSF can be absorbed as part of the circulatory system. Shunt systems come in a variety of models, and typically share similar functional components. These components include a ventricular catheter which is introduced through a burr hole in the skull and implanted in the patient's ventricle, a drainage catheter that carries the CSF to its ultimate drainage site, and optionally a flow-control mechanism, e.g., shunt valve, that regulates the one-way flow of CSF from the ventricle to the drainage site to maintain normal pressure within the ventricles. The ventricular catheter typically contains multiple holes or pores positioned along the length of the ventricular catheter to allow the CSF to enter into the shunt system. To facilitate catheter insertion, a removable rigid stylet, situated within the lumen of the ventricular catheter, is used to direct the catheter toward the desired targeted location. Alternatively, or in addition, blunt tip brain cannulas and peel-away sheaths have been used to aid placement of the catheters.

One common problem encountered with the use of ventricular catheters is the difficulty in measuring the pressure within the patient's ventricle. One current technique involves placing a pressure sensor in line with the catheter and external to the ventricles such that the sensor communicates with the cerebrospinal fluid flowing through the catheter. As the pressure drop across the catheter is negligible, the sensor can measure pressure that resembles the intra-ventricular pressure. While this technique is advantageous in that it allows the use of a relatively large sensor, catheter blockage can impede the pressure sensed by the sensor, thus preventing an accurate measurement of intra-ventricular pressure from being obtained.

Accordingly, there remains a need for a catheter having a pressure sensor that is effective to accurately measure a patient's ventricular pressure.

SUMMARY OF THE INVENTION

The present invention generally provides methods and devices for measuring pressure, and more preferably for measuring the intra-ventricular pressure. The methods and devices are particularly advantageous in that they provide a sensor assembly that is hermetically sealed, thereby allowing the device to be permanently implanted, and that can be effective to directly measure the intra-ventricular pressure, thus avoiding potentially inaccurate readings due to blockages occurring in the catheter.

In one embodiment, a pressure sensing catheter is provided having an elongate body with an inner lumen extending at least partially therethrough, and at least one fluid-entry port formed therein in fluid communication with the inner lumen. A distal portion of the catheter can include a pressure sensor having at least a portion that is exposed to an external environment surrounding the elongate body such that the pressure sensor is effective to measure a pressure of the external environment. In an exemplary embodiment, the pressure sensor is positioned distal to the fluid-entry port(s). The catheter can also include an antenna that is coupled to the pressure sensor and that is adapted to communicate a measured pressure from the pressure sensor to an external device.

The pressure sensor can be coupled to the catheter using a variety of techniques. In certain exemplary embodiments, the pressure sensor can be mated to an external surface of the distal portion of the elongate body, or it can be disposed within a recess formed in an external surface of the elongate body. In other exemplary embodiments, the pressure sensor can be embedded within the elongate body, and the elongate body can include an opening formed therein for exposing at least a portion of the pressure sensor to an external environment. In yet another exemplary embodiment, the pressure sensor can be embedded within a distal tip of the elongate body, and a portion of the pressure sensor can protrude beyond the distal tip of the elongate body to measure a pressure of an external environment. In other aspects, the pressure sensor can be disposed within the inner lumen of the elongate body, and the elongate body can include an opening formed therein for exposing at least a portion of the pressure sensor to an external environment. In yet another embodiment, the elongate body can include a second inner lumen extending therethrough, and the pressure sensor can be disposed within the second inner lumen of the elongate body. In this embodiment, the elongate body preferably includes an opening formed therein and extending into the second inner lumen for exposing at least a portion of the pressure sensor to an external environment.

The antenna that is coupled to the pressure sensor can also have a variety of configurations, and it can be disposed within, embedded within, positioned around, or positioned external to the catheter. In one exemplary embodiment, the antenna is in the form of a coil and it is disposed within the lumen of the catheter or a second lumen formed in the catheter, embedded within the catheter, or disposed around the catheter. In another exemplary embodiment, the antenna can be separate from or external to the catheter to allow the antenna to be positioned a distance apart from the catheter. The antenna can, however, be coupled to the catheter by a connector that extends from the antenna to the catheter to connect the antenna to the pressure sensor.

In other aspects, at least a portion of the pressure sensing catheter can include a biocompatible fluid-impermeable coating for hermetically sealing the pressure sensor, the antenna, and/or a connector extending between the pressure sensor and the antenna. In one exemplary embodiment, the pressure sensor, antenna, and the connector extending therebetween can be coated to form a hermetically sealed sensor assembly. In other embodiments, only a portion of the pressure sensor, the antenna, and/or the connector can be coated. For example, a portion of the pressure sensor that is configured to be exposed to fluid during use can be coated. In yet another embodiment, the catheter can be coated such that any portion of the pressure sensor, the antenna, and the connector exposed to an external environment are coated. Where the catheter is coated, the fluid-entry ports formed in the catheter are preferably clear from any coating that would otherwise prevent fluid flow therethrough. The particular coating used can also vary, but in one exemplary embodiment the coating is a solvent-based silicone.

Exemplary methods for measuring intra-ventricular pressure are also provided. In one embodiment, a distal portion of a catheter having a pressure sensor is positioned within a patient's ventricle, and an antenna coupled to the pressure sensor is positioned adjacent to a patient's scalp. The antenna can be coupled directly to the catheter, or it can be separate from and external to the catheter while still maintaining communication with the sensor. A reading of a ventricular pressure surrounding the catheter can then be obtained from the pressure sensor, and the reading can be communicated, e.g., telemetrically, to an external device.

Methods for manufacturing intra-ventricular pressure sensor devices are also provided. In one exemplary embodiment, a catheter is formed having a distal end with a pressure sensor. At least a portion of the pressure sensor can be exposed to an external environment such that the pressure sensor is adapted to measure a pressure surrounding the catheter. The catheter can also include an inner lumen extending therethrough, at least one fluid-entry port formed therein and in fluid communication with the inner lumen, an antenna coupled to the pressure sensor and adapted to communicate a measured pressure to an external device, and a connector extending between the pressure sensor and the antenna.

The catheter can have a variety of configurations, and the particular methods for manufacturing the catheter can vary depending on the configuration. For example, the method for manufacturing the catheter can vary depending on whether the antenna is disposed within, embedded within, disposed around, or positioned external to the catheter. Where the antenna is external to the catheter, in one exemplary embodiment the catheter can be extruded with the connector disposed therein and extending from the catheter to couple to the antenna. Alternatively, where the antenna is embedded within the catheter, the catheter can be extruded with the antenna and at least a portion of the connector disposed therein. In other embodiments, the connector can be disposed within a slot formed in a sidewall of the catheter and extending along at least a portion of the length thereof. The method of manufacturing the catheter can also vary depending on the configuration of the pressure sensor. In one exemplary embodiment, the catheter can include a bullet-shaped tip that is coupled to a distal end thereof, and at least a portion of the pressure sensor can be disposed within the bullet-shaped tip. In another exemplary embodiment, the catheter can be manufactured by coupling the antenna, connector, and pressure sensor to form a sensor assembly, coating the sensor assembly such that it is fluid-impermeable, and coupling the sensor assembly to the catheter. The sensor assembly can be coupled to the catheter by, for example, attaching the sensor assembly to an external surface of the catheter, or positioning some of all of the sensor assembly in cut-outs, slots, or recesses formed in the catheter.

In another exemplary embodiment, an implantable valve is provided having a valve assembly disposed therein for controlling a rate of fluid flow through a valve housing, and having a sensor disposed therein for measuring a pressure of fluid flow through the valve housing. The sensor can have a variety of configurations, but in one embodiment the sensor can be coupled to an antenna that is adapted to communicate a sensed pressure to an external reading device. In an exemplary embodiment, the sensor and antenna are coated with a fluid-impermeable coating.

In another embodiment, the sensor can be disposed within a pressure sensor assembly, and the pressure sensor assembly can be disposed within the valve housing in fluid communication with a valve inlet and valve outlet. The pressure sensor assembly can include, for example, a domed portion defining a reservoir therein, and the sensor can be adapted to measure a pressure of fluid flowing through the reservoir. In one exemplary embodiment, the pressure sensor assembly can include an inlet tube adapted to receive fluid flowing into the valve inlet, and an outlet tube adapted to deliver fluid to the valve outlet. The valve assembly can be disposed between the outlet tube of the pressure sensor assembly and the valve outlet.

In other aspects, the pressure sensor assembly can include a needle guard disposed therein and positioned between the domed portion and the sensor. The needle guard can be adapted to protect the sensor from a needle being inserted through the domed portion. In one exemplary embodiment, the needle guard can include an opening formed therein and adapted to expose a portion of the sensor to fluid flowing through the reservoir. In another embodiment, the pressure sensor assembly can include a washer that is adapted to seat the sensor. The sensor can be coupled to a coiled antenna that is adapted to be received within a central opening formed in the washer.

An exemplary method for measure ventricular pressure is also provided and includes positioning a distal end of a ventricular catheter within a patient's ventricle, coupling a proximal end of the ventricular catheter to a valve inlet formed on an implantable valve, and coupling a valve outlet formed on the valve to a drainage catheter such that fluid flows from the ventricle through the valve to the drainage catheter. A rate of fluid flowing through the valve can be controlled by a valve assembly disposed within the implantable valve. The method can also include obtaining a pressure measurement of the pressure flowing through the valve using a pressure sensor disposed within the valve. In an exemplary embodiment, wherein the pressure measurement is obtained telemetrically by positioning a reading device in proximity to the valve.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention generally provides methods and devices for measuring pressure, and preferably for measuring an intra-ventricular pressure. The methods and devices are particularly advantageous in that they provide a hermetically sealed pressure sensing assembly that allows the device to be effective for long term or permanent implantation. In certain exemplary embodiment, the methods and devices are also particularly advantageous in that they can be effective to obtain a direct measurement of the intra-ventricular pressure, thereby avoiding potentially inaccurate readings due to a blockage occurring in the ventricular catheter. A person skilled in the art will appreciate that, while the device is described in connection with a ventricular catheter for measuring the intra-ventricular pressure, the device can be used for a variety of medical procedures to measure the pressure in a variety of cavities.

In one exemplary embodiment, the present invention provides a pressure sensing catheter having a pressure sensor and an antenna that is coupled to the pressure sensor, e.g., by a connector. The pressure sensor can be adapted to measure a pressure surrounding the catheter, and the antenna can be adapted to telemetrically communicate the measured pressure to an external device. In an exemplary embodiment, the antenna, pressure sensor, and/or connector are hermetically sealed by the catheter and/or a coating to prevent the antenna, pressure sensor, and connector from coming into contact with fluid, thereby allowing the catheter to be permanently implanted or otherwise used for long term use. The catheter and/or coating are also particularly effective to prevent damage to the components due to the corrosive in-vivo environment. The catheter and/or coating should not, however, interfere with the ability of the pressure sensor to sense the pressure of fluid in contact therewith. Exemplary catheter configurations are discussed in the various embodiments described and illustrated herein, however a person having ordinary skill in the art will appreciate that the pressure sensing catheter can have a variety of other configurations. Moreover, the pressure sensor, antenna, and connector can be incorporated into virtually any catheter or other device.

Figure 1:
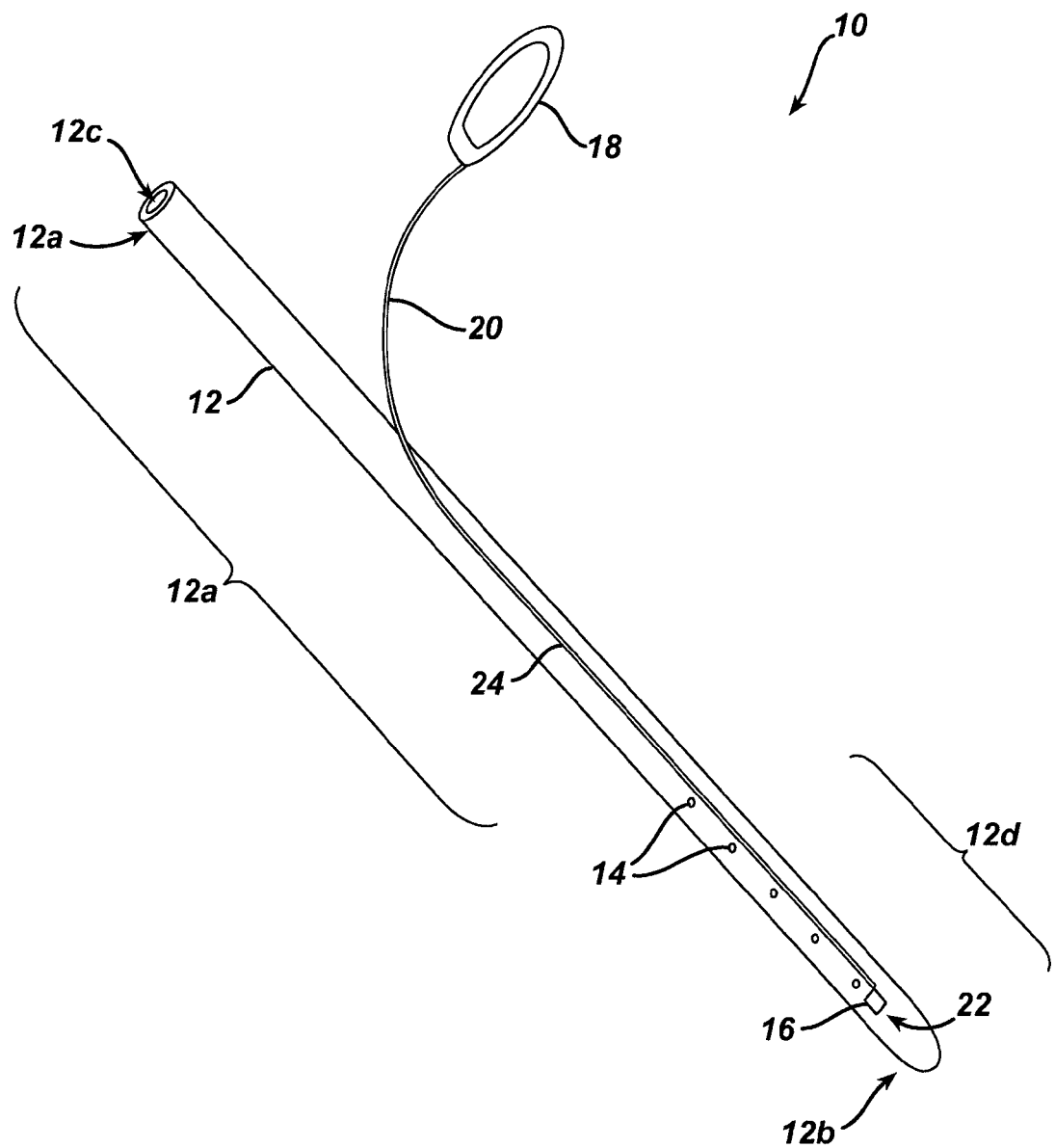
FIG. 1 is a perspective view of one exemplary embodiment of a pressure sensing catheter having an external antenna.

FIG. 1 illustrates one exemplary embodiment of a pressure sensing catheter 10. As shown, the catheter 10 has a generally elongate body 12 with proximal and distal ends 12a, 12b and an inner lumen 12c extending therethrough for accommodating fluid flow. The inner lumen 12c preferably terminates just proximal to the distal end 12b such that the distal end 12b is closed. The proximal end 12a can be open and it can be adapted to couple to another medical device, such as a valve for controlling fluid flow from the catheter 10. The catheter 10 can also include at least one fluid-entry port 14 formed in a sidewall thereof and extending into the inner lumen 12c. The location, quantity, and size of the fluid-entry ports 14 can vary, but they should be adapted to allow fluid to flow therethrough and into the inner lumen 12c.

The elongate body 12 that forms the catheter 10 can have virtually any configuration, shape, and size. Preferably, the elongate body 12 has a length l that is sufficient to allow at least the distal portion 12d to be implanted in a patient's ventricles, while the proximal portion 12p can extend therefrom to connect to another medical device, such as a valve. The elongate body 12 can also be formed from a variety of materials. In an exemplary embodiment, however, the body 12 is formed from a flexible, biocompatible material. Suitable materials include, for example, polymers such as silicones, polyethylene, and polyurethanes, all of which are known in the art. The body 12 can also optionally be formed from a radio-opaque material. A person skilled in the art will appreciate that the materials are not limited to those listed herein and that a variety of other biocompatible materials having the appropriate physical properties to enable the desired performance characteristics can be used.

As is further shown in FIG. 1, the catheter 10 also includes a pressure sensor 16 that is adapted to measure a pressure of an external environment, e.g., the pressure in the ventricle, surrounding the catheter 10, and an antenna 18 that is adapted to communicate the measured pressure to an external device. The pressure sensor 16 and the antenna 18 can be coupled to one another using a variety of techniques, but in the embodiment shown in FIG. 1 a connector 20 extends between the pressure sensor 16 and the antenna 18.

Figure 2:
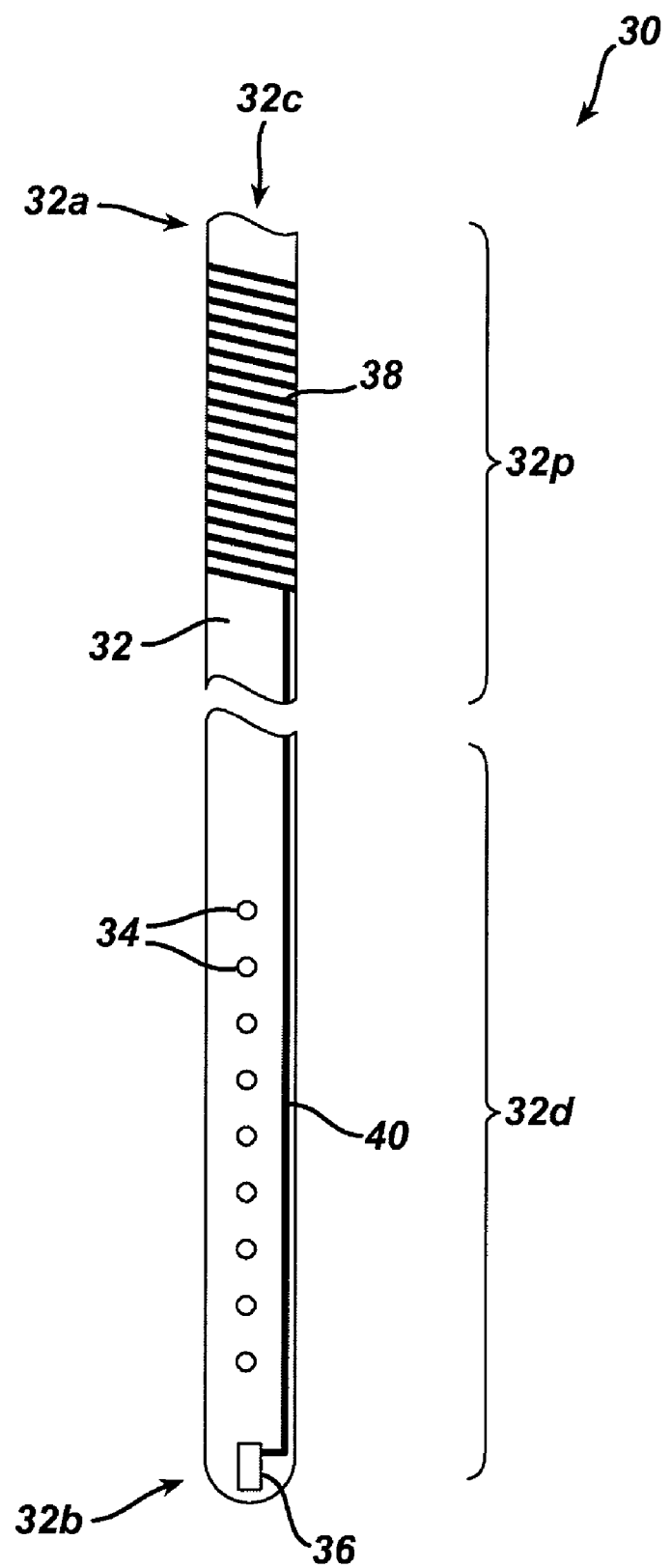
FIG. 2 is a cross-sectional view of another exemplary embodiment of a pressure sensing catheter having an internal antenna.
Figure 8:
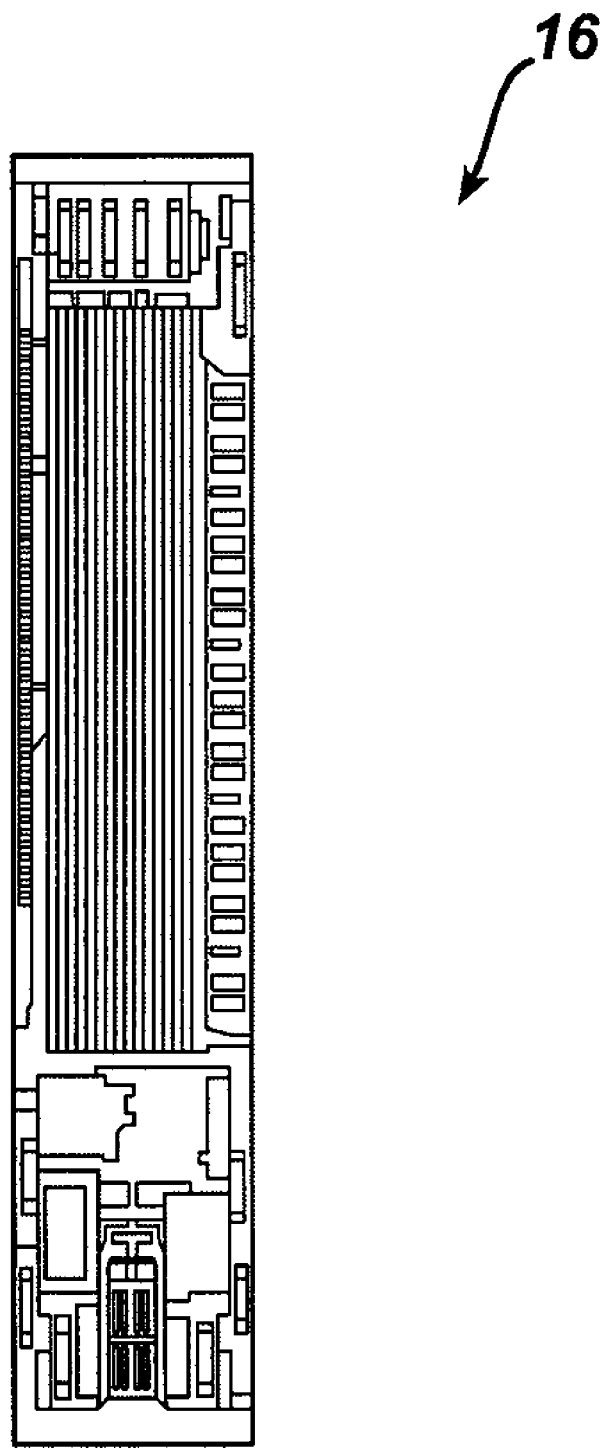
FIG. 8 is a top view of an exemplary embodiment of a pressure sensor.
Figure 9A:
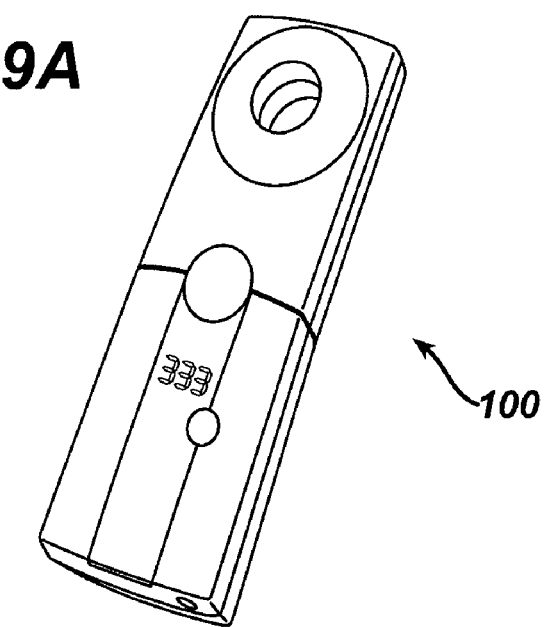
FIG. 9A is a perspective view of an exemplary embodiment of an external radiofrequency telemetry system.
Figure 9B:
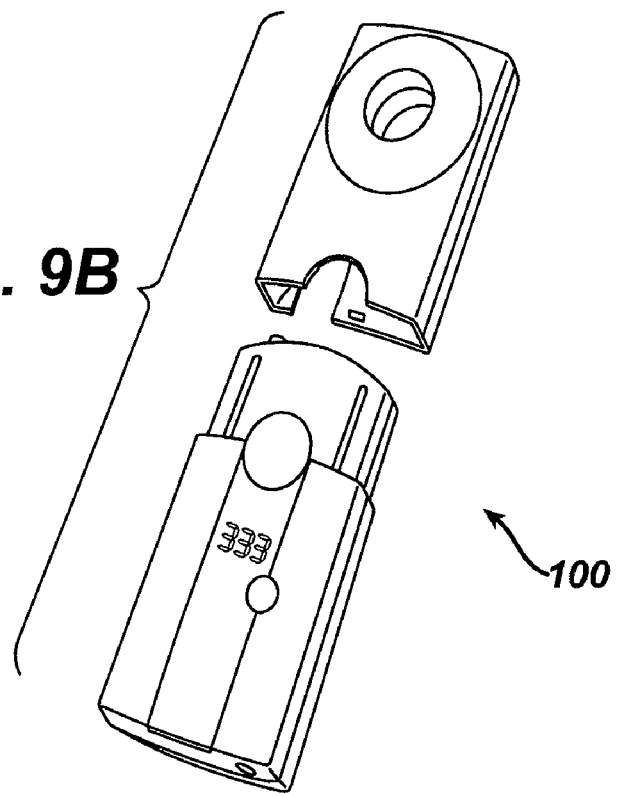
FIG. 9B is a perspective view of the external radiofrequency telemetry system of FIG. 9A in a disassembled configuration.

Exemplary embodiments of a pressure sensor 16, connector 20, and antenna 18 are described in more detail in U.S. Pat. No. 5,321,989, U.S. Pat. No. 5,431,057, and EP Patent No. 1 312 302. These references are hereby incorporated by reference herein in their entirety. In general, the pressure sensor 16 can be formed on a microchip, as shown in FIG. 8. The size of the pressure sensor 16 can vary, but in one exemplary embodiment the pressure sensor 16 has a length of about 7 mm and a width of about 1 mm. The connector 20 that mates the pressure sensor 16 to the antenna 18 can also vary, but in an exemplary embodiment the connector 20 is a gold wire or other conductive element. The antenna 18 can also have a variety of configurations, but in an exemplary embodiment the antenna 18 preferably has a coil-shaped configuration. In particular, as shown in FIG. 1, the antenna 18 is formed into a substantially circular coil. Another embodiment of an antenna 38 is shown in FIG. 2, and in that embodiment the antenna 38 is wrapped around the elongate body 12 to form a substantially cylindrical coil. The coil configuration will allow the antenna 18, 38 to function with an external device, such as the radio-frequency telemetry device 100 shown in FIGS. 9A and 9B. The telemetry device is described in more detail in EP Patent No. 1 312 302.

Continuing to refer to FIG. 1, the particular configuration of the pressure sensor 16, connector 20, and antenna 18 with respect to the catheter 10 can vary. In the embodiment shown in FIG. 1, the pressure sensor 16 is disposed within a cut-out or recess 22 formed in the elongate body 12 adjacent to the distal end 12b. The recess 22 can extend partially through the elongate body 12, or it can extend fully through the elongate body 12 such that it is in communication with the inner lumen 12c. The position of the recess 22 can vary, but in an exemplary embodiment the recess 22 is formed distal of the distal-most fluid entry port 14. Such a configuration allows the pressure sensor 16 to be fully positioned within the ventricle to obtain an accurate reading.

As further shown in FIG. 1, the connector 20 is disposed within an elongate slot 24 formed in the elongate body 12 and extending proximally from the recess 22. A proximal portion of the connector 20 extends from the elongate slot 24 to mate to the antenna 18. As shown, the antenna 18 is not attached to the elongate body 12, but rather it is separate from the elongate body 12 and it is coupled to a proximal end of the connector 20. Such a configuration allows the antenna 18 to be positioned a distance apart from the elongate body 12. For example, when the pressure sensing catheter 10 is implanted in a patient's ventricle, the antenna 18 can be positioned just underneath the patient's scalp. This will allow an external device to be placed adjacent to the antenna 18 to telemetrically communicate with the antenna 18 and receive a pressure reading obtained by the pressure sensor 16, as will be discussed in more detail below. The elongate slot 24 also allows the connector 20 and antenna 18 to optionally be separated from the elongate body 12 if necessary. For example, the antenna 18 may need to be positioned a particular distance away from the elongate body 12, or the elongate body 12 may need to be trimmed, in which case an additional portion of the connector 20 can be removed from the slot 24.

As indicated above, the pressure sensor 16, connector 20, antenna 18, and/or the elongate body 12 can also include a coating that is adapted to hermetically seal all or at least a portion of the pressure sensor 16, connector 20, and antenna 18. The coating can be applied to only a portion of the pressure sensor 16, connector 20, and antenna 18 that will be exposed to fluid within the patient's ventricle, or it can be applied to each of the pressure sensor 16, connector 20, antenna 18, and optionally the elongate body 12. In the embodiment shown in FIG. 1, the pressure sensor 16, connector 20, and antenna 18, hereinafter collectively referred to as the sensor assembly, are preferably pre-coated prior to coupling the sensor assembly to the elongate body 12. Once coated the pressure sensor 16 can be positioned within the recess 22 and the connector 20 can be positioned within the slot 24. An adhesive or other mating technique can optionally be used to affix the pressure sensor 16 within the recess 22, and optionally to affix the connector 20 within the slot 24. Any adhesive or other mating technique can be used to attach the connector 20 to the elongate body 12, however, if desirable it should be configured to allow the connector 20 to be torn away from the body 12 if necessary.

Alternatively, or in addition to pre-coating, the catheter 10 can be coated after the sensor assembly is coupled to the elongate body 12 to form a protective sheath over the sensor assembly. The fluid-entry ports 14 should, however, either be protected from any coating applied thereto, formed after the coating is applied, or be cleared of any coating applied thereto to allow fluid to flow therethrough and into the inner lumen 12c. In other embodiments, only certain components of the sensor assembly can be coated. A person skilled in the art will appreciate that a variety of other techniques can be used to hermetically seal the pressure sensor 16, connector 20, and antenna 18.

The material used to form the coating can vary, and a variety of techniques can be used to apply the coating. By way of non-limiting example, suitable materials include polyurethane, silicone, solvent-based polymer solutions, and any other polymer that will adhere to the components to which it is applied to, and suitable techniques for applying the coating include spray-coating or dip-coating.

FIG. 2 illustrates another exemplary embodiment of a pressure sensing catheter 30. The catheter 30 is similar to catheter 10 in that it includes an elongate body 32 having proximal and distal ends 32a, 32b with an inner lumen 32c extending therebetween, and several fluid entry ports 34 formed in a distal portion 32d of the elongate body 32 and in fluid communication with the inner lumen 32c to allow fluid to flow therethrough. The catheter 30 also includes a pressure sensor 36 that is disposed within the distal end 32b of the elongate body 32 and a connector 40 that extends from the pressure sensor 36 to mate to an antenna 38. The pressure sensor 36 and connector 40 can be coupled to the elongate body 32 as previously described, or they can have a variety of other configurations as will be described in more detail with respect to FIGS. 3-7B.

The embodiment shown in FIG. 2 differs from the embodiment shown in FIG. 1 in that the antenna 38 is not separate from and external to the elongate body 32, but rather it is coupled to a proximal portion 32p of the elongate body 32. In particular, the antenna 38 is formed into a cylindrical-shaped coil and is embedded within the elongate body 32. This can be achieved by molding the elongate body 32 around the antenna 38. Preferably, the connector 40 is coupled to the antenna 38 and is also molded within the elongate body 32. In other embodiments, the antenna 38 can be wrapped around the elongate body 32 or it can be disposed within the inner lumen 32c of the elongate body 32. An adhesive can optionally be used to fix the antenna 18 to the elongate body 12. In use, as will be discussed in more detail with respect to FIG. 11, the antenna 38, which is disposed in the proximal portion 32p of the elongate body 32, can be positioned outside of the ventricle and adjacent to the patient's scalp to allow a reading to be obtained from the pressure sensor 32 via the antenna 38. Accordingly, in an exemplary embodiment, the antenna 38 should be positioned at a location on the elongate body 32 that allows for such positioning of the antenna 38 during use.

As previously discussed with respect to FIG. 1, the catheter 30 can also include a coating applied to the pressure sensor 36, antenna 38, connector 40, and/or the elongate body 32. In an exemplary embodiment, the coating is only applied to the pressure sensor 36, or at least to the portion of the pressure sensor 36 that is exposed to the external environment, as the catheter forms a seal around the connector 40 and antenna 38 that are embedded therein. For example, the pressure sensor 36 can be disposed within a recess formed in the elongate body 32 and the coating can be applied over the recess to seal the pressure sensor 36 therein.

FIGS. 3-7B illustrate a variety of other configurations for the pressure sensor and connector with respect to the elongate body. While not shown, the antenna coupling to the pressure sensor and connector can be coupled to the catheter, or it can be separate from and external to the catheter. While the pressure sensor and connector can have a variety of configurations, in certain exemplary embodiments the pressure sensor and/or connector can be positioned within the inner lumen of the elongate body, positioned within a second inner lumen in the elongate body, embedded in the elongate body, disposed on an external surface of the elongate body, and/or positioned external to the elongate body. A coating can be applied to the pressure sensor and/or connector, however the particular technique used to hermetically seal the pressure sensor and connector in each embodiment can depend on the configuration of the pressure sensor and connector, as well as the antenna (shown in FIGS. 1 and 2), and whether the antenna is internal or external to the elongate body. Exemplary methods for manufacturing each embodiment and for hermetically sealing the pressure sensor and connector are also disclosed. A person skilled in the art will appreciate that the pressure sensing catheter can have a variety of configurations, and that the method for manufacturing the pressure sensing catheter can vary depending on the configuration.

Figure 3:
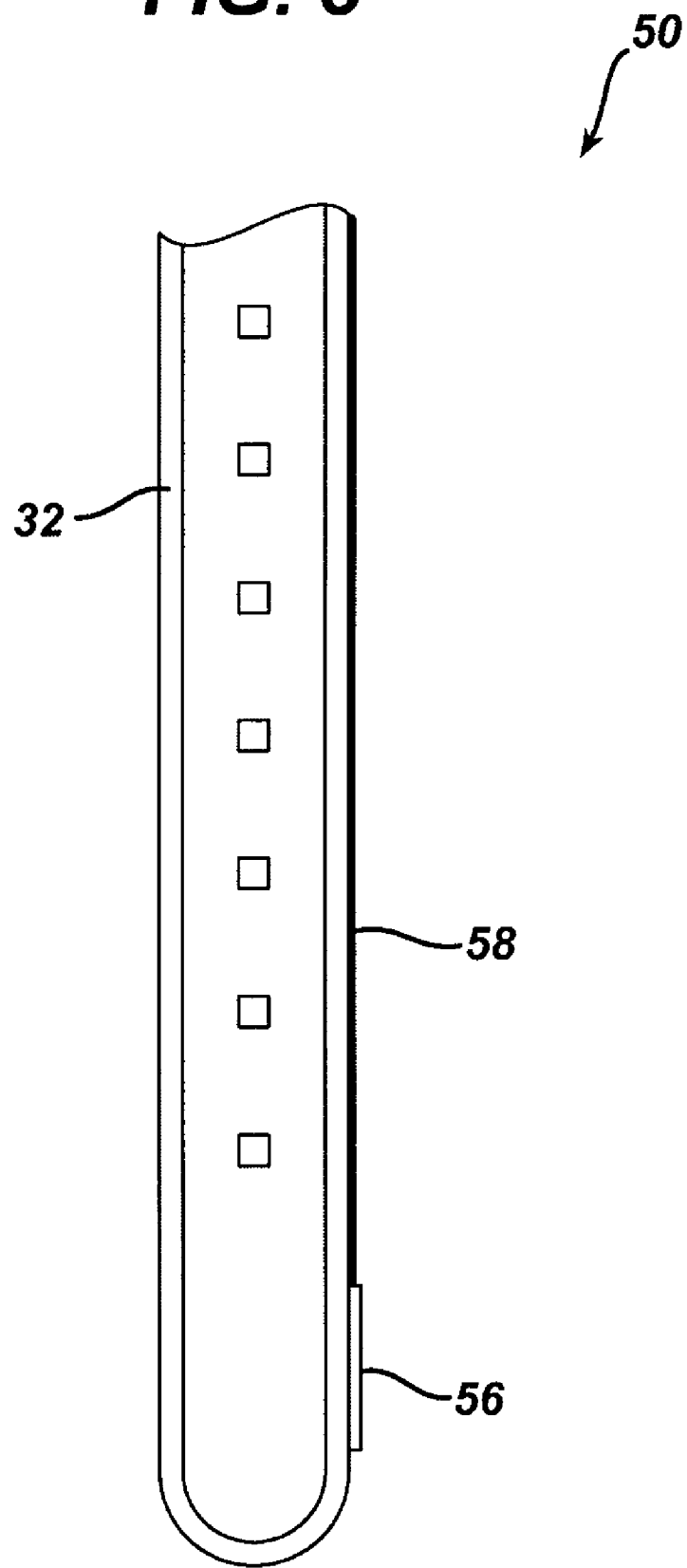
FIG. 3 is a cross-sectional view of one embodiment of a distal portion of a pressure sensing catheter having a pressure sensor disposed on an external surface thereof.

FIG. 3 illustrates a distal portion 50 of an elongate body 52 of a pressure sensing catheter. In this embodiment, the pressure sensor 56 and the connector 58 are disposed on an external surface of the elongate body 52. An adhesive or any other mating technique can be used to attach the pressure sensor 56 and connector 58 to the body 52. In order to protect the sensor 56 and connector 58 from fluid damage, a coating can be applied to some or all of the device, as previously described. For example, the sensor assembly can be pre-coated prior to coupling the sensor assembly to the elongate body 52. Alternatively, or in addition, a coating can be applied to the elongate body 52 after the sensor assembly is coupled thereto. The fluid-entry ports should, of course, be free from any coating to allowing fluid to flow therethrough.

Figure 4:
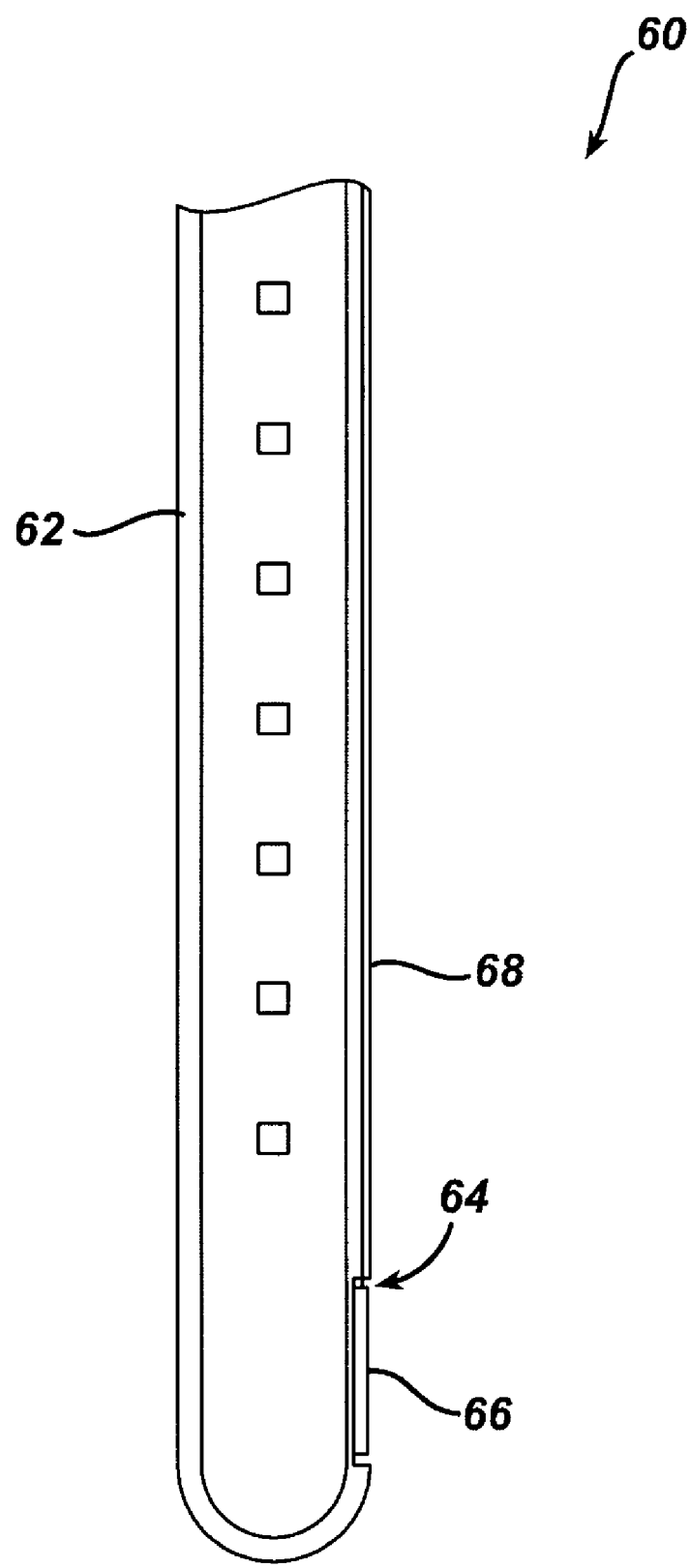
FIG. 4 is a cross-sectional view of another embodiment of a distal portion of a pressure sensing catheter having a pressure sensor disposed within a recess formed therein.

FIG. 4 illustrates another embodiment of a distal portion 60 of an elongate body 62 of a pressure sensing catheter. In this embodiment, which is similar to the embodiment shown in FIG. 1, the pressure sensor 66 is disposed within a recess 64 formed in the elongate body 62, and the connector 68 is embedded within the elongate body 62. The connector 68 can be embedded in the elongate body 62 during molding, and the recess 64 can either be molded into the elongate body 62 or it can be cut out of the elongate body 62 after the elongate body 62 is formed. The sensor 66 can thereafter be positioned within the recess 64. As previously discussed, an adhesive or any other mating technique can be used to retain the pressure sensor 66 within the recess 64. A coating can be applied to the pressure sensor 66 prior to and/or after disposing the pressure sensor 66 in the recess 64. The coating can optionally be applied to the elongate body 62 to seal the pressure sensor 66 within the recess 64.

Figure 5:
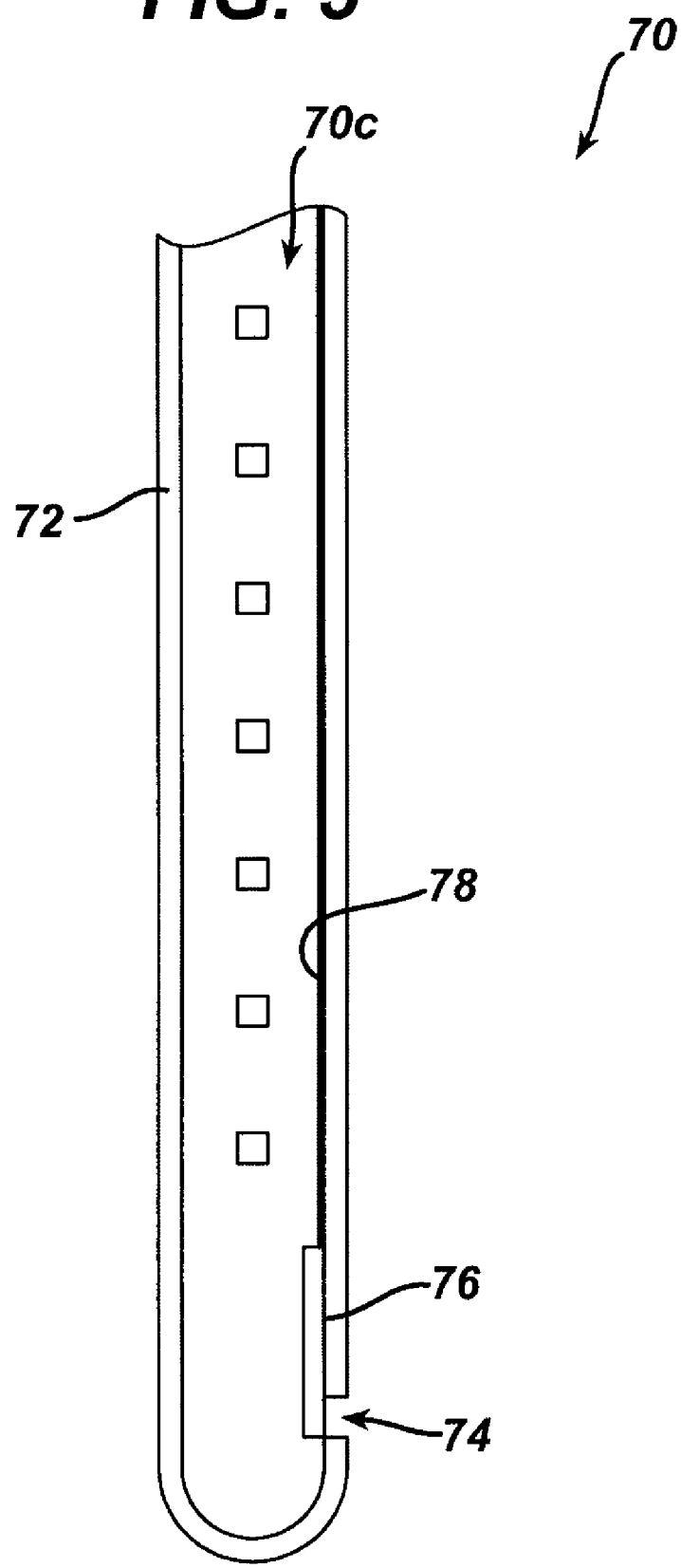
FIG. 5 is a cross-sectional view of yet another embodiment of a distal portion of a pressure sensing catheter having a pressure sensor disposed within an inner lumen formed therein, and having a window formed therein for exposing a portion of the pressure sensor to an external environment.

FIG. 5 illustrates yet another embodiment of a distal portion 70 of an elongate body 72 of a pressure sensing catheter. In this embodiment, the pressure sensor 76 and the connector 78 are disposed within the inner lumen 70c of the elongate body 72. A cut-out or window 74 is formed in the elongate body 72 to expose a portion of the pressure sensor 76 that is adapted to measure the pressure surrounding the catheter. A coating is preferably disposed over the sensor assembly before it is disposed within the elongate body 72, and an adhesive of other mating technique can be used to attach the sensor assembly to the elongate body 72. A coating can optionally be applied to the window 74.

Figure 6:
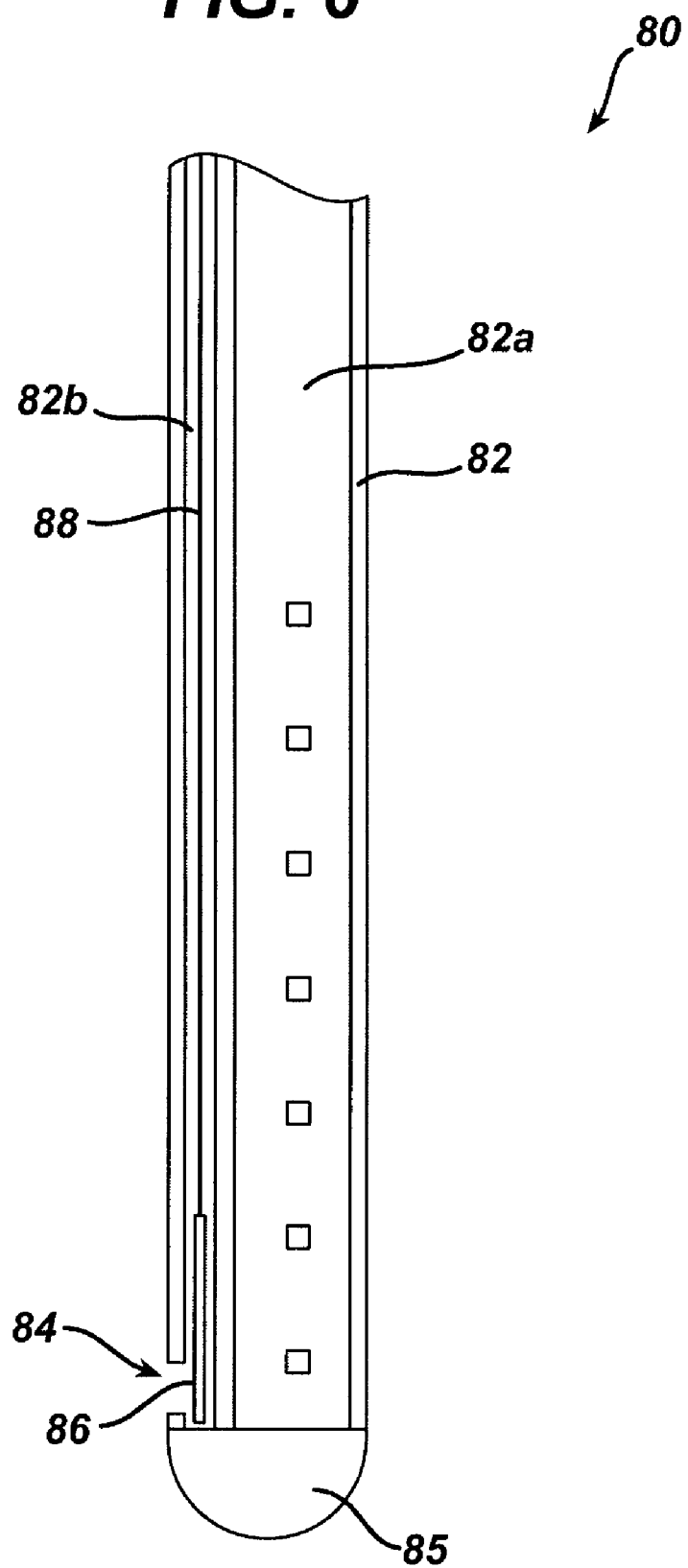
FIG. 6 is a cross-sectional view of another embodiment of a distal portion of a pressure sensing catheter having a pressure sensor disposed within a second lumen formed in the catheter.

FIG. 6 illustrates another embodiment of a distal portion 80 of an elongate body 82 of a pressure sensing catheter. In this embodiment, the elongate body 82 includes first and second inner lumens 82a, 82b, and the pressure sensor 86 and the connector 88 are disposed within the second inner lumen 82b. A cut-out or window 84 is formed in the elongate body 82 and is in communication with the second inner lumen 82b to expose a portion of the pressure sensor 86 that is adapted to measure the pressure surrounding the catheter. A coating can either be disposed over the sensor assembly before it is disposed within the second inner lumen 82b in the elongate body 82, or a coating can be applied to the window 84 to seal the pressure sensor 86 and connector 88 within the elongate body 82.

Figure 7A:
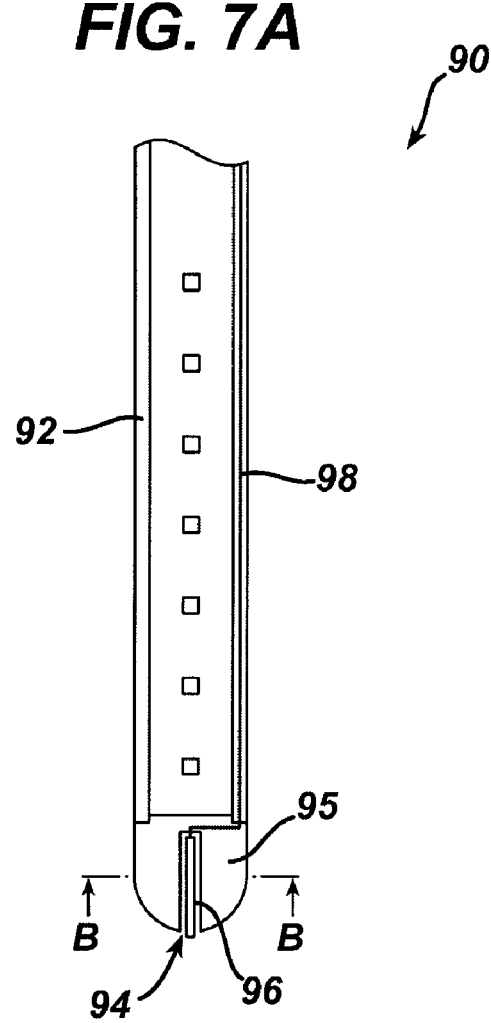
FIG. 7A is a cross-sectional view of yet another embodiment of a distal portion of a pressure sensing catheter having a pressure sensor disposed within a distal tip of the catheter.
Figure 7B:
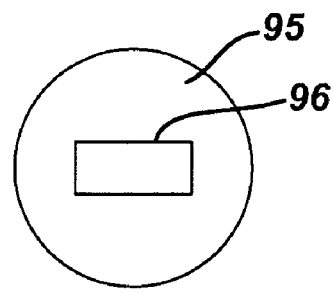
FIG. 7B is a cross-sectional view of the distal tip of the catheter show in FIG. 7A taken across line B-B.

FIGS. 7A and 7B illustrate another embodiment of a distal portion 90 of an elongate body 92 of a pressure sensing catheter. In this embodiment, the pressure sensor 96 is disposed within a bullet-shaped tip 95 that is attached to the elongate body 92. The bullet-shaped tip 95 and elongate body 92 can be manufactured as separate components and then coupled to one another to couple the pressure sensor 96 to the connector 98. As shown in FIGS. 7A and 7B, the pressure sensor 96 is disposed within a recess 94 formed in the distal-most end of the bullet-shaped tip 95, however a portion of the pressure sensor 96 preferably extends from the recess 94 to allow the external pressure to be measured. An adhesive can be used to retain the pressure sensor 96 within the tip 95, and a coating can be applied to the pressure sensor 96 and/or the tip 95. As is further shown in FIG. 7A, the elongate body 92 can be formed with the connector 98 embedded therein. An adhesive or other mating technique can then be used to attach the bullet-shaped tip 95 to the open distal end of the elongate body 92. The connector 98 disposed within the elongate body 92 can then be coupled to the pressure sensor 96 in the tip 95. Various techniques can be used to achieve a connection. For example, a portion of the connector 98 can be embedded or disposed within the tip 95 and connected to the pressure sensor 96 when the pressure sensor 96 is inserted into the recess 94. The two portions of the connector 98 can then be mated to one another when the tip 95 is attached to the elongate body 92. Alternatively, the recess can extend completely through the distal tip 92 to allow a portion of the connector 98 extending from the elongate body 92 to be connected to the pressure sensor 96. As previously discussed, various techniques can be used to hermetically seal the pressure sensor 96, connector 98, and antenna (shown in FIGS. 1 and 2).

Figure 10:
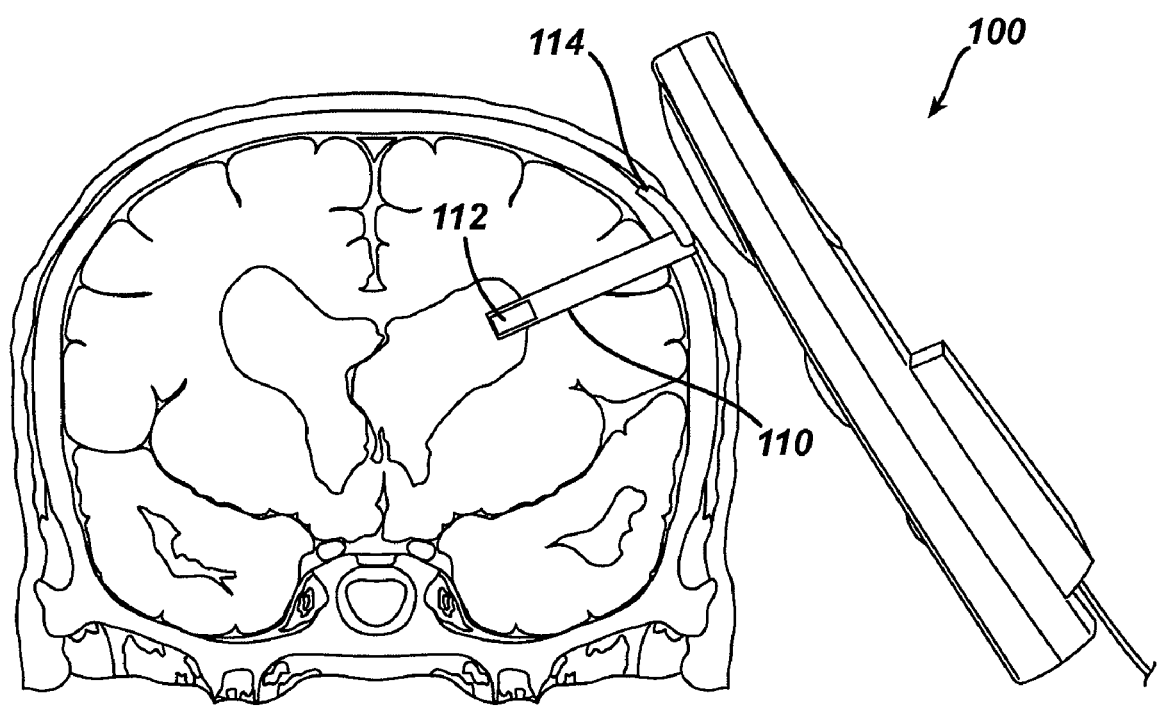
FIG. 10 is a cross-sectional view of a human brain showing one embodiment of a ventricular catheter having a distal portion implanted in the ventricle and having an external antenna positioned under the patient's scalp.
Figure 11:
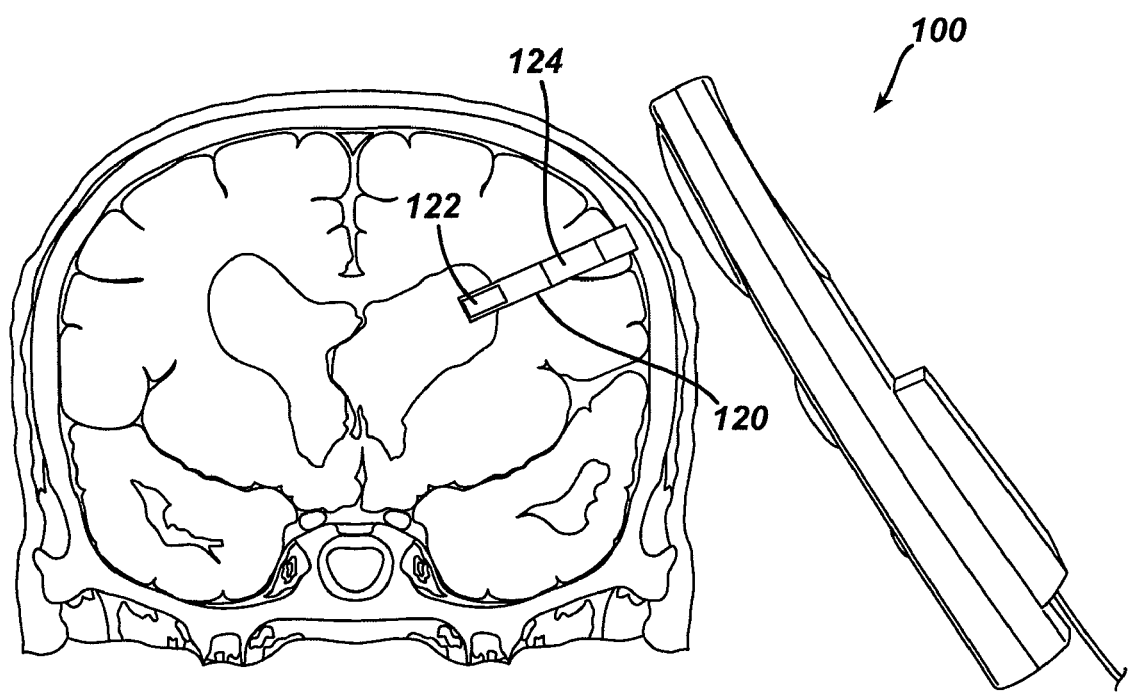
FIG. 11 is a cross-sectional view of a human brain showing one embodiment of a ventricular catheter having a distal portion implanted in the ventricle and having an internal antenna positioned under the patient's scalp.

FIGS. 10 and 11 shown exemplary methods for using a pressure sensing catheter. Referring first to FIG. 10, a pressure sensing catheter 110 is shown having a pressure sensor 112 (labeled "chip") disposed within the distal end thereof, and an external antenna 114 (labeled "coil") positioned a distance apart from a proximal end thereof. As shown, the catheter 110 is positioned in the patient's ventricle, and the external antenna 114 is positioned just beneath just beneath the patient's scalp. The pressure sensor 112, which is exposed to the fluid surrounding the catheter 110, can measure the ventricular pressure surrounding the catheter 110. An external device 100, as shown, can then be positioned adjacent to the antenna 114 to telemetrically communicate with the antenna 114, and thereby obtain a reading of the measured pressure.

FIG. 11 similarly illustrates a pressure sensing catheter 120 having a pressure sensor 112 disposed within a patient's ventricle for measuring the intra-ventricular pressure. In this embodiment, the antenna 124 is internal to the catheter 120, however it is still positioned just beneath the patient's scalp. The device 120 therefore functions in the same manner described above with respect to FIG. 10.

A person skilled in the art will appreciate that, while the pressure sensor assembly is shown and described in connection as being disposed within a distal portion of a ventricular catheter, the pressure sensor assembly can be disposed at a variety of other locations and in a variety of other devices. Multiple pressure sensor assemblies can also be used, and they can be disposed at various locations relative to one another. The use of multiple pressure sensor assemblies can be particularly advantageous as it can allow a differential pressure of the system to be obtained. The differential pressure of the system should be equal to the operating pressure of the system, thus indicating whether the system is performing properly.

Figure 12A:
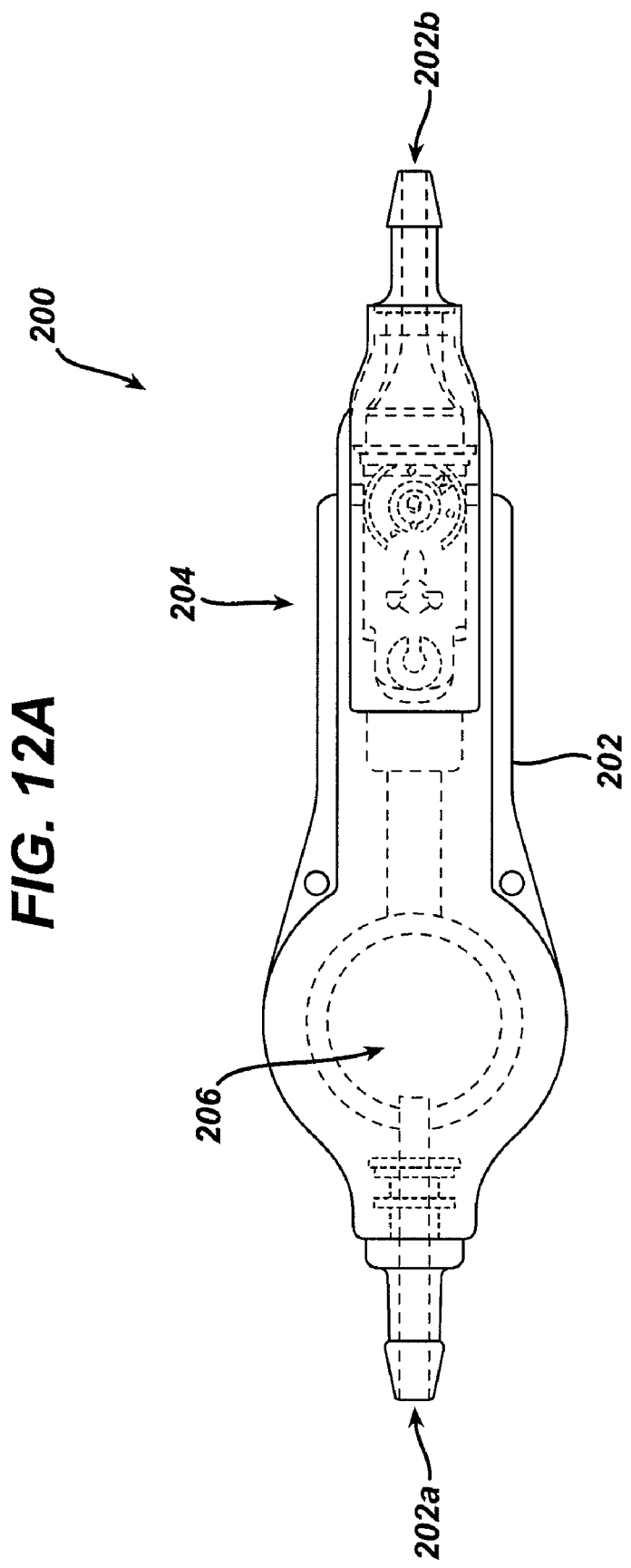
FIG. 12A illustrates another embodiment of a pressure sensor that is disposed within an implantable valve.
Figure 12B:
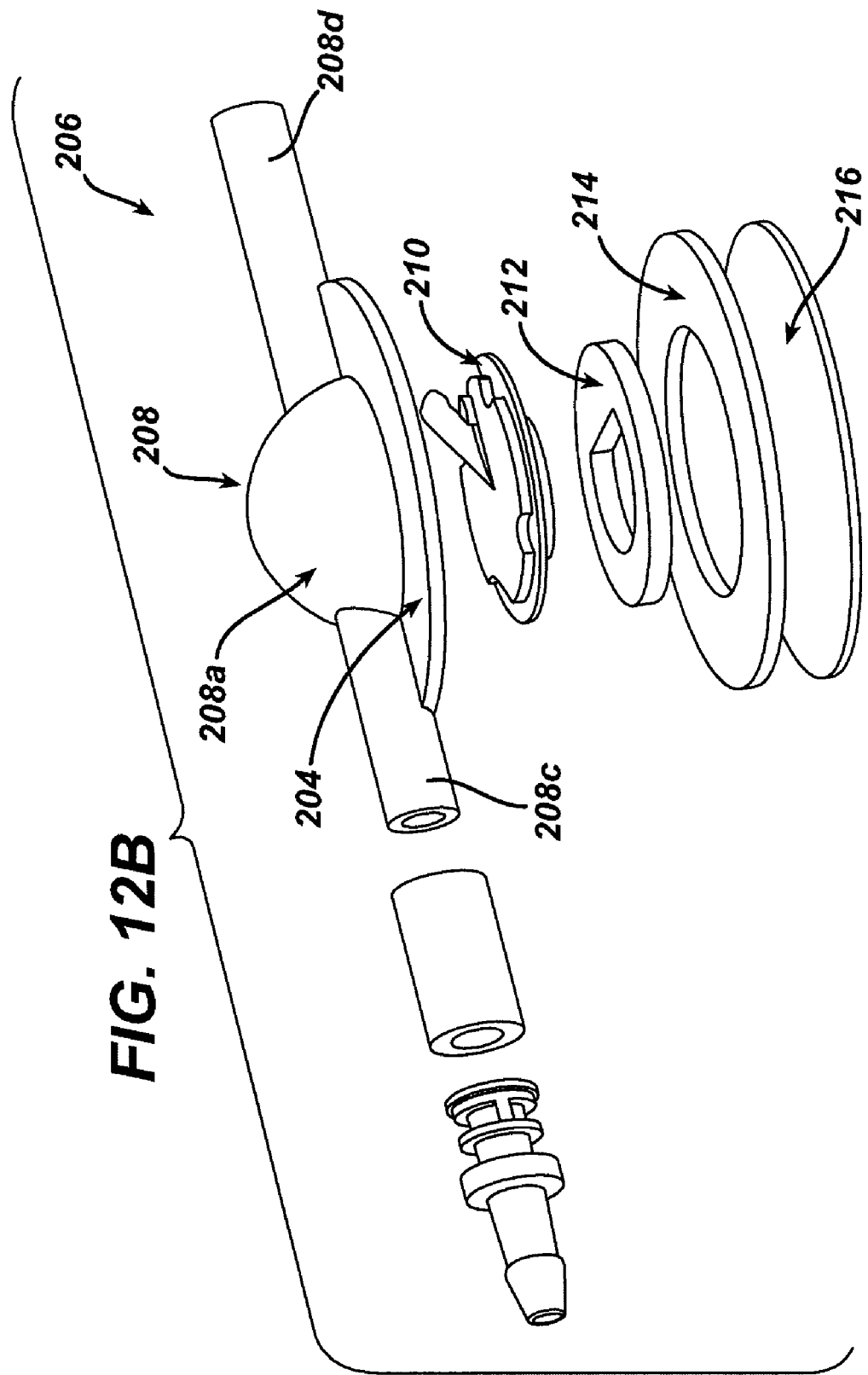
FIG. 12B illustrates an exploded view of a portion of the implantable valve shown in FIG. 12A.

FIGS. 12A and 12B illustrate another exemplary embodiment of a pressure sensor assembly that is disposed within a valve housing of an implantable valve 200 that can be used to control fluid flow. As indicated above, the exemplary valve 200 can be used alone or in combination with a pressure sensor assembly that is disposed in the distal portion of the ventricular catheter, and/or other pressure sensor assemblies disposed upstream or downstream of the valve 200.

While the implantable valve 200 can have virtually any configuration, and a variety of implantable valves known in the art can be used, FIG. 12A illustrates an implantable valve 200 having valve housing 202 with an inlet 202a and an outlet 202b. The valve housing 202 can contain a valve mechanism 204 for controlling the flow of fluid from the inlet 202a to the outlet 202b, and a pressure sensor assembly 206 for measuring a pressure of the fluid flowing through the valve 200, as will be described in more detail with respect to FIG. 12B. While the valve mechanism 204 and pressure sensor assembly 206 of the valve 200 are shown in-line with one another and with the inlet 202a and outlet 202b, and the pressure sensor assembly 206 is positioned upstream of the valve 200, the valve 200 can have a variety of other configurations and the valve mechanism 204, pressure sensor assembly 206, inlet 202a, and outlet 202b can be positioned at various locations relative to one another. For example, the inlet 202a can extend at a right angle with respect to the pressure sensor assembly 206 such that the inlet 202a extends in a direction substantially transverse to a longitudinal axis of the valve 200. The valve mechanism 210 can also have a variety of configurations. By way of non-limiting example, exemplary valves are described in U.S. Pat. Nos. 3,886,948, 4,332,255, 4,387,715, 4,551,128, 4,595,390, 4,615,691, 4,772,257, and 5,928,182, all of which are hereby incorporated by reference.

An exemplary pressure sensor assembly 206 is shown in more detail in FIG. 12B, and as shown the pressure sensor assembly 206 can include a sensor housing 208, a sensor 212, and a backing 216. The illustrated pressure sensor assembly 206 also includes a needle guard 210 and a washer 214, as will be discussed in more detail below.

The sensor housing 208 can have a variety of shapes and sizes, but in the illustrated exemplary embodiment the sensor housing 208 has a generally hemi-spherical or domed portion 208a that defines a pumping reservoir therein. The sensor housing 208 can also include an inlet tube 208c that couples to the inlet 202a of the valve 200, and an outlet tube 208d that couples to the outlet 202b of the valve 200. When the sensor housing 208 is mated to the backing 206, the reservoir chamber defined by the housing 202 is sealed, thereby allowing fluid to flow from the inlet 202a of the valve 200, through the sensor housing 208, through the valve 210, and out the outlet 202b in the valve 200. The sensor housing 208 can also include a flange 208b formed around a base of the domed portion 208a to allow the device to be secured to tissue. For example, the flange 208b can include one or more suture holes formed therein for receiving suture to attach the flange 208b to tissue.

As mentioned above, the sensor housing 206 can include a sensor 212 disposed therein. The sensor 212, which is similar to sensor 16 shown in FIG. 8, can be formed on a microchip which can be coupled to an antenna for communicating a sensed pressure to an external device. As shown in FIG. 12B, the antenna has a substantially circular shape, and the microchip sensor is coupled to the antenna which can, for example, be in the form of a gold microcoil. The sensor 212 can also include a fluid-impermeable coating disposed therearound, as previously described, to protect the sensor from fluid flowing through the sensor housing 208. While the sensor 212 can be similar to sensor 16, the size of the sensor 212 can be larger than the size of sensor 16 due to the size of the housing 208. The size will vary depending on the valve 200, but in one exemplary embodiment the microchip sensor 212 has a size that is in the range of about 1 mm to 3 mm, and more preferably that is about 2.5 mm$^2$. As previously indicated, exemplary embodiments of a pressure sensor and antenna are described in more detail in U.S. Pat. No. 5,321,989, U.S. Pat. No. 5,431,057, and EP Patent No. 1 312 302.

In use, the sensor 212, which is disposed within the sensor housing 208, is adapted to measure the pressure of fluid flowing through the sensor housing 208. In particular, the inlet 202a of the valve 200 can be coupled to a ventricular catheter for receiving fluid flow from the ventricles, and the outlet 202b can be coupled to a drainage catheter. As the fluid enters the sensor housing 208, the pressure of the fluid will apply a force to active sensor membranes formed on the sensor 212, thereby allowing the fluid pressure to be measured. The sensed pressure can be communicated, via the antenna, to an external reading device, such as device 100 shown in FIGS. 9A and 9B.

As previously mentioned, and as further shown in FIG. 12B, the sensor assembly 206 can also include a washer 214. The washer 214 can be provided to seat the sensor 212, such that the washer 214 and sensor 212 are positioned against the backing 216. The washer 214 can also be configured such that the sensor 212 is sub-flush with the washer 214. Such a configuration may protect the sensor 212 from potential damage when the domed portion 208a of the housing 208 is depressed to pump fluid through the housing 208, or to otherwise test the valve or clear the valve from debris, etc.

As further shown in FIG. 12B, the sensor assembly 206 can also include a needle guard 210 for protecting the sensor 212. In particular, the needle guard 210 can protect the sensor 212 from coming into contact with the domed portion 208a of the housing 208 when the domed portion 208a is depressed, as the needle guard 210 can be positioned between the sensor 212 and the domed portion 208a. The needle guard 210 can also be provided to protect the sensor from a needle being inserted through the domed portion 208a of the sensor housing 208, thereby preventing potential damage to the sensor 212. A needle may be used to deliver or withdraw fluid from the sensor housing 208. While the shape of the needle guard 210 can vary depending on the shape of the sensor assembly 206, in an exemplary embodiment, as shown, the needle guard 210 has a substantially planar, circular shape and it is adapted to be disposed between the domed portion 208a of the housing 208 and the sensor 212. The needle guard 210 can, however, include an opening formed therein and positioned adjacent to the microchip sensor 212 to allow fluid flowing through the sensor housing 208 to come into contact with the sensor 212. In an exemplary embodiment, a flange or protective member is disposed over the opening, without blocking the opening from fluid flow, to prevent a user from accidentally inserted a needle through the opening. A person skilled in the art will appreciate that a variety of other techniques can be used to protect the sensor 212.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for measuring ventricular pressure, comprising:
    positioning a distal end of a ventricular catheter within a patient's ventricle;
    coupling a proximal end of the ventricular catheter to a valve inlet formed on an implantable valve having a valve assembly and a pressure sensor disposed therein, and coupling a valve outlet formed on the valve to a drainage catheter such that fluid flows from the ventricle through the implantable valve to the drainage catheter, wherein a rate of fluid flowing through the valve is controlled by the valve assembly disposed within the implantable valve; and
    obtaining a pressure measurement of the fluid flowing through the valve using the pressure sensor disposed within the valve, wherein the pressure sensor is located upstream of the valve assembly within the valve and thus the pressure measurement is made prior to the fluid flowing into the valve assembly.

2. The method of claim 1, further comprising obtaining the pressure measurement telemetrically by positioning a reading device in proximity to the valve.

3. The method of claim 2, wherein the pressure sensor is formed on a microchip that is coupled to an antenna that communicates the pressure measurement to the reading device.

4. The method of claim 1, wherein the pressure sensor is in-line with the valve assembly.

5. The method of claim 1, wherein the pressure sensor is disposed within a domed portion of the valve, the domed portion defining a reservoir therein, and wherein the pressure sensor obtains a pressure measurement of the pressure flowing through the reservoir in the domed portion.

6. The method of claim 5, further comprising inserting a needle through the domed portion of the valve, wherein a needle guard protects the pressure sensor from coming into contact with the needle when the needle is inserted into the domed portion.

7. The method of claim 5, further comprising depressing the domed portion of the valve to pump fluid through the reservoir.

8. The method of claim 1, further comprising suturing at least one flange on the implantable valve to tissue to secure the implantable valve to tissue.

9. A method for measuring ventricular pressure, comprising:
    implanting an implantable valve beneath a patient's scalp, the implantable valve having a pressure sensor assembly disposed therein for sensing pressure of a flow of fluid passing therethrough, and a valve assembly disposed therein for regulating the flow of fluid through the implantable valve, the pressure sensor assembly being distal of the valve assembly;
    positioning a distal end of a ventricular catheter coupled to an outlet of the valve in a patient's ventricle;
    coupling a valve outlet formed on the implantable valve to a drainage catheter such that fluid flows from the ventricle, through the pressure sensor assembly of the implantable valve, through the valve assembly of the implantable valve, and to the drainage catheter; and
    positioning an external device adjacent to the patient's scalp to telemetrically communicate with an antenna disposed within the implantable valve and thereby obtain a reading of a pressure of fluid flowing through the implantable valve and measured by a pressure sensor disposed within the pressure sensor assembly and coupled to the antenna.

10. The method of claim 9, further comprising depressing a domed portion of the implantable valve to pump fluid therethrough, the pressure sensor being disposed within a reservoir defined by the domed portion.

* * * * *